United States Patent [19]

Smith

[11] 3,989,386
[45] Nov. 2, 1976

[54] AUTOMATED INSPECTION APPARATUS AND METHOD

[75] Inventor: Charles W. Smith, Bethel Park, Pa.

[73] Assignee: GTE Sylvania Incorporated, Stamford, Conn.

[22] Filed: Jan. 15, 1975

[21] Appl. No.: 541,234

[52] U.S. Cl. .............................. 356/156; 356/167
[51] Int. Cl.² ........................................ G01N 21/30
[58] Field of Search .................. 250/571, 572, 235; 356/156, 167, 168

[56] References Cited
UNITED STATES PATENTS

| | | | |
|---|---|---|---|
| 3,361,029 | 1/1968 | Russell et al. ...................... | 356/167 |
| 3,636,362 | 1/1972 | Beeman et al. ..................... | 356/167 |
| 3,645,626 | 2/1972 | Druschel ............................ | 356/167 |
| 3,744,905 | 7/1973 | Smith ................................ | 356/156 |
| 3,883,251 | 5/1975 | Helava .............................. | 250/571 |

*Primary Examiner*—John K. Corbin
*Assistant Examiner*—Richard A. Rosenberger
*Attorney, Agent, or Firm*—Norman J. O'Malley; Lawrence R. Fraley; Donald R. Castle

[57] ABSTRACT

There is disclosed an automatic apparatus for sequentially inspecting a plurality of selected areas of an apertured material. The apparatus comprises a light determination means including an established light source and a positioned light detection means, a movable retention means for retaining the apertured material, and a control means for actuating the light determination means and the movable retention means whereby the selected areas of the apertured material will be sequentially positioned between the light source and the light detection means whereupon light is projected through each of said areas. The light passing through the areas is detected by said light detection means. A method for inspecting is also disclosed.

15 Claims, 4 Drawing Figures

AUTOMATED INSPECTION APPARATUS AND METHOD

BACKGROUND OF THE INVENTION

This invention relates to automated inspection apparatus and more specifically to apparatus for automatically inspecting apertured material. Even more particularly, this invention relates to an automatically operated apparatus for inspecting aperture masks for eventual utilization in color television cathode ray tubes.

The conventional aperture mask found in most color television cathode ray tubes is positioned within the envelope of the tube in spaced relationship to an adjacent cathodoluminescent screen formed on the inner surface of the tube face panel. The primary reason for the mask is to insure that electron beams emitted from electron guns positioned in the neck of the tube strike the proper phosphor dots found in the cathodoluminescent screen to provide the correct color combinations while not allowing the electron beams to overlap and strike other dots.

Aperture masks, as described above, are made from sheets of very thin metal, usually steel, and contain thousands of very small apertures or holes through which the electron beams are passed before striking the phosphor dots. These holes are usually etched out of the metal through the employment of photographic and etching techniques standard in the industry. After photoprinting the hole pattern onto the mask surfaces, the etching solutions are sprayed on to remove the exposed areas. After etching, the masks are still integral parts of a long metal strip or web. Individual masks are cut from this strip and formed to coincide with the internal portion of the cathode ray tube screen.

Typical examples of the sizes of holes in aperture masks may range from 0.005 to 0.014 inch and have center to center spacings ranging from 0.02 to 0.03 inch depending on the overall size of the mask and corresponding picture tube. Additionally, many of the newer varieties of today's picture tubes employ masks having elongated or slotted apertures therein.

It can be readily seen, therefore, that the size of these apertures are critical in order that proper electron beam-phosphor dot combinations occur. To assure that these critical dimensions are maintained during the manufacture of these masks, various methods of inspection have been employed. One such method has been for a human inspector to examine the mask, utilizing some means of magnification. Not only has this method proven time consuming, but the possibility for human error is ever present. A further more advanced method of inspection has been to employ a frame having several reading heads which read various points on the masks as they move on the production line. While substantially eliminating the human error possibility, this method also requires undesirable time consumption, primarily because it is necessary to clamp each of these reading heads to the masks at these points. Still another method is illustrated in U.S. Pat. No. 3,744,905 wherein a pair of light detectors receives the light transmitted through the moving mask line by a corresponding pair of light sources positioned on an opposite side of the line. While this apparatus serves effectively to calibrate the aperture sizes in the mask over a broad range, it is incapable of selectively monitoring aperture sizes at several designated locations on the mask without requiring substantial modification. When utilizing the plural nozzle etching sprayers typically found in today's aperture mask production, this selective capability by the inspecting apparatus would in turn permit adjustment to only one or a few of the etchers, thus providing a more precisioned end product.

It is believed therefore that an apparatus and method capable of automatically inspecting designated areas on apertured material to determine the relative sizes of the apertures within said material would constitute an advancement in the art.

OBJECTS AND SUMMARY OF THE INVENTION

It is, therefore, a primary object of this invention to provide an apparatus and method for inspecting selected areas on apertured metallic material to accurately determine the relative sizes of the apertures within said material.

It is a further object of this invention to provide an apparatus having the capabilities described above which is totally automatic in operation.

The foregoing objects are achieved in one aspect of the present invention by the provision of an automated inspection apparatus for sequentially inspecting a plurality of selected areas of an apertured metallic material to determine the relative sizes of the apertures within said material. The apparatus comprises a light determination means having an established light source and a positioned light detection means, a movable retention means for moving the metallic material in a predetermined pattern, and a control means for automatically actuating the retention means and light determination means. The mentioned retention means fixedly retains the metallic material between the light source and light detection means and moves the material in accordance with said predetermined pattern whereby each of the selected areas of the metallic material will be sequentially positioned between the light source and light detection means. Accordingly, the light source as described will project light to one side of each of the selected materials and the light detection means will detect the light passing through the material when the selected areas are positioned between said light source and light detection means.

The foregoing objects are achieved in another aspect of the invention by the provision of a method for sequentially inspecting a plurality of selected areas of an apertured metallic material to determine the relative sizes of the apertures within said material. The method utilizes an apparatus having a light determination means which includes an established light source and a positioned light detection means, and a movable retention means. Accordingly, the method comprises the steps of positioning the apertured metallic material whereby said material will occupy a singular plane, actuating the described retention means to move the apertured material in accordance with a predetermined pattern of direction whereby each of the selected areas will be sequentially positioned between the light source and light detection means, and actuating the light determination means whereby the light source will project a defined column of light to one side of each of the selected areas and the light detection means will detect the light passing through these areas when said areas are positioned between said light source and light detection means.

DETAILED DESCRIPTION OF THE PREFERRED EMBODIMENTS

For a better understanding of the present invention, together with other and further objects, advantages, and capabilities thereof, reference is made to the following disclosure and appended claims in connection with the above-described drawings.

Figure 1:
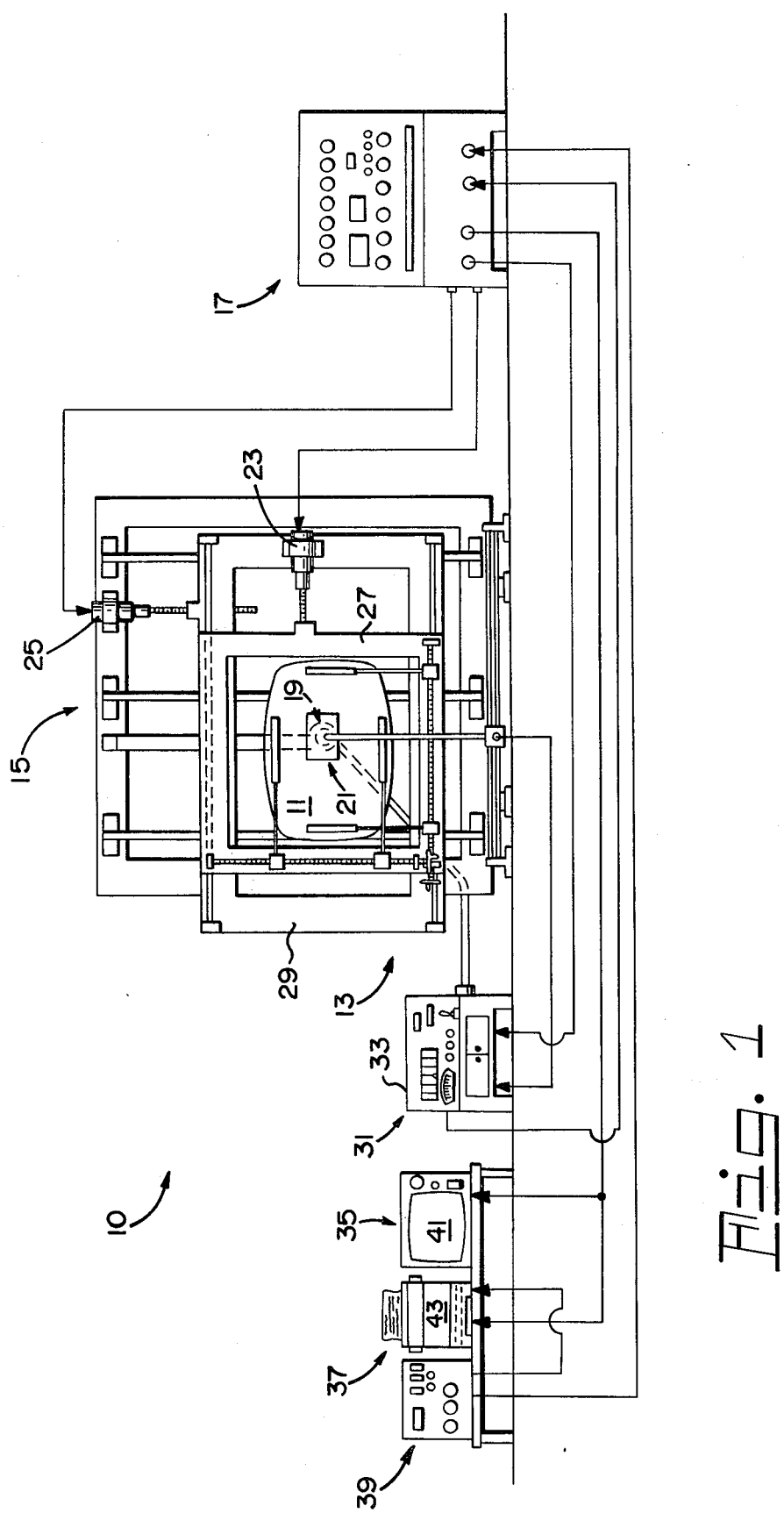
FIG. 1 is an overall layout view of the apparatus in accordance with a preferred embodiment of the present invention.

With particular reference to FIG. 1, there is illustrated an automated inspection apparatus 10 in accordance with a preferred embodiment of the present invention. Inspection apparatus 10 is adapted for sequentially inspecting a plurality of selected areas of an apertured metallic material 11 to determine the relative sizes of the apertures within said material. In the preferred embodiment of the invention, inspection apparatus 10 comprises a light determination means 13, a movable retention means 15, and a control means 17.

Figure 2:
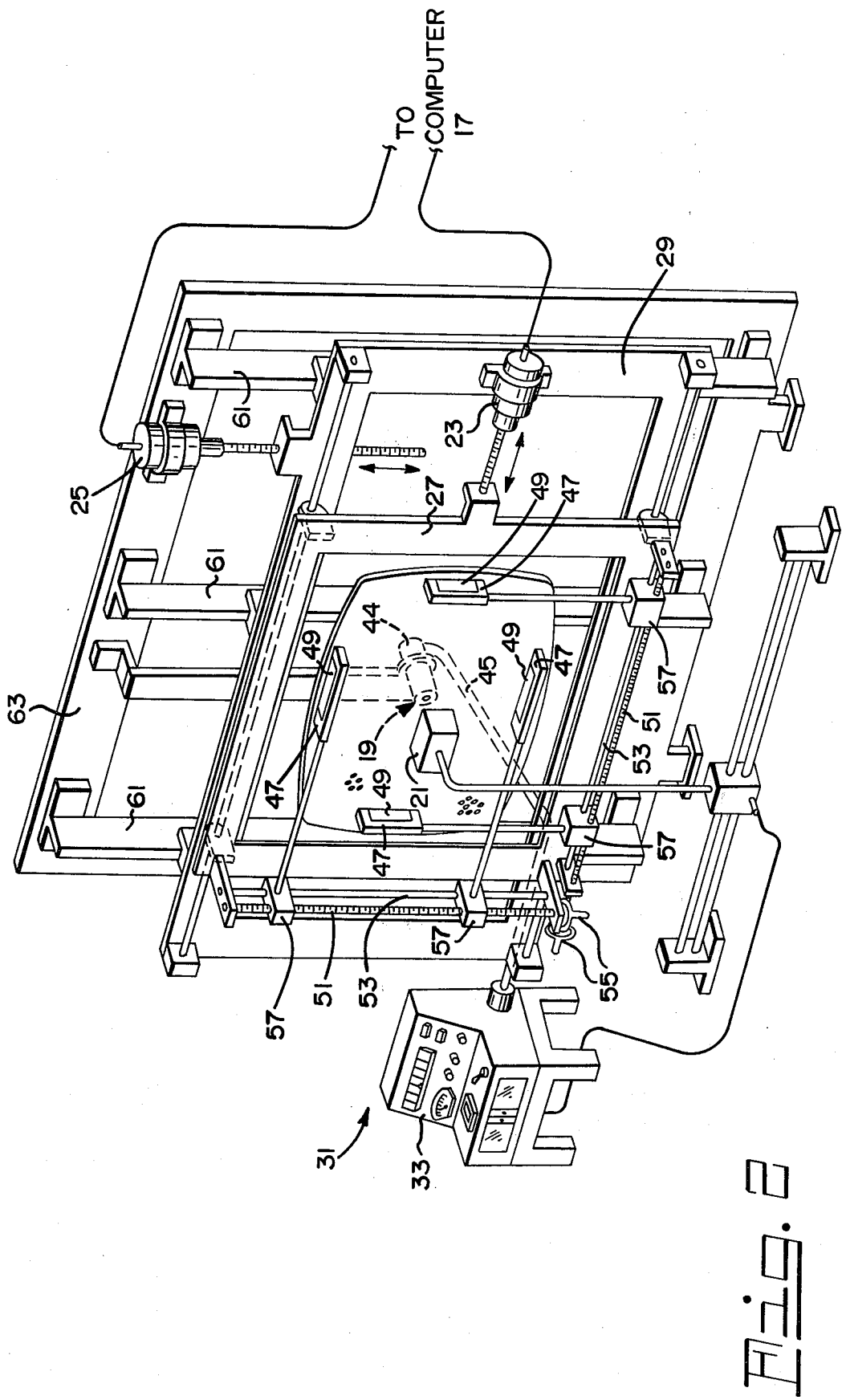
FIG. 2 is an isometric view of a preferred embodiment of the movable retention means and light determination means of the present invention.

Apertured metallic material 11 is fixedly retained within movable retention means 15 of inspection apparatus 10 in a manner to be more fully illustrated in FIG. 2. Once positioned therein, metallic material 11 is moved in accordance with a predetermined pattern in order that each of the selected areas to be inspected will be sequentially positioned between an established light source 19 (shown hidden) for projecting a defined column of light to one side of material 11 and a positioned light detection means 21. Light source 19 and detection means 21 form part of the aforementioned light determination means 13. Accordingly, it is the function of retention means 15 to move apertured metallic material 11 between light source 19 and light detection means 21 in the manner described. The aforementioned movement is achieved through actuation of a pair of corresponding drive means 23 and 25 which in turn serve to move a corresponding pair of movable frame members 27 and 29. Each of the aforementioned drive means 23 and 25 is operatively connected to control means 17 and is actuated in accordance with signals received therefrom.

As illustrated in FIG. 1, light determination means 13 further comprises a responsive means 31. In the preferred embodiment of the invention, responsive means 31 comprises a digital voltmeter 33 which in turn is operatively and electrically connected to light detection means 21. Responsive means 31 is further operatively connected to control means 17 for being actuated to interrogate light detection means 21 which in turn detects the light passing through material 11. Accordingly, when digital voltmeter 33 receives an electrical signal from light detection means 21 upon reading one of the described selected areas on material 11, voltmeter 31 supplies a representative first electrical signal to control means 17.

As further illustrated in FIG. 1, inspection apparatus 10 additionally comprises an output means 35, a reporting means 37, and a manually actuated control station 39. It is to be understood that the last three mentioned components are utilized in the present invention primarily for auxiliary functioning capabilities. That is, in the broader aspects of the present invention, inspection apparatus 10 need only comprise the described light determination means 13, movable retention means 15, and control means 17.

In the preferred embodiment of the invention, control means 17 comprises an IBM System 7 electronic computer, available from the IBM Corporation, Armonk, New York, under the Ser. No. 10688. Control means 17 is electrically connected to the other illustrated components of the present invention in the manner as detailed and is adapted for providing a second electrical signal to output means 35 and reporting means 37, said second signal representative of said first signal from means 13. Reporting means 37 is also electrically joined to control station 39. As has been described, both responsive means 31 and manual control station 39 are electrically connected to control means 17 and adapted for providing an electrical signal thereto.

The preferred components for output means 35 and reporting means 37 are a television 41 and an electric typewriter 43, respectively. As can be understood, television 41 is adapted for providing a visual readout across the face of its cathode ray tube upon being electrically energized by the described signal from control means 17. Additionally, typewriter 43 is adapted for providing a typed report upon being energized by manual control station 39. Once energized, typewriter 43 provides a report in accordance with a signal received from control means 17. It is to be understood that the aforementioned electrical connections are relatively basic in nature and can easily be accomplished by an electrical technician of reasonable skill. Therefore, further definition of the electrical interconnections between the control means 17, drive means 23 and 25, light determination means 13, output means 35, recording means 37, and control station 39 is not believed necessary.

In operation, the apertured metallic material 11 is positioned on movable retention means 15 in the manner to be more adequately described within the description of FIG. 2. With material 11 fixedly retained, it is preferred to position light source 19 and light detection means 21 opposite each other at the approximate center of material 11. This is not essential to the operation of inspection apparatus 10, however, but is preferred to facilitate programming of electronic computer 17. The operator of inspection apparatus 10 next depresses a start button at manually actuated control station 39. This in turn provides a manually triggered input signal to control means 17 whereupon the control means responds by signalling television 41. The resulting visual output indicates to the operator that performance of the next function can now be accomplished. In other words, the computer is indicating to the operator that it is in the proper functioning phase and is prepared to receive input from station 39. The corresponding readout on the cathode ray tube of television 41 instructs the operator to now provide the computer, via manual switching, with the corresponding parameters related to apertured metallic material 11. In the case of aperture masks for color television cathode ray tubes, the sizes of the mask material varies according to the size of the tube in which it is to be positioned. Accordingly, each individual metallic material 11 is required to have a corresponding job number.

Upon providing computer 17 with the necessary input information e.g. job number, the computer electronically searches its files and actuates a pair of translation members, each operatively connected to the aforementioned drive means 23 and 25 respectively. These translation members (not shown) are preferably electrical buffer translators which translate the respective signals from computer 17 to the drive means. This in turn results in actuation of drive means 23 and 25 to move material 11 accordingly. As the drive means are correspondingly actuated to move material 11 in accordance with the planned predetermined patterns, an output signal is provided the computer from responsive means 31 of light determination means 13 at each reading of the chosen selected areas on the material. The computer is capable of comparing each of the received values as determined by light determining means 13, and thereafter providing an output indicative of this comparison in the form of a second electrical signal to output means 35. This in turn results in a visual output being displayed across the face of the television's cathode ray tube. The operator of apparatus 11 then has only to make a comparison with the visual readings as provided. This relative comparison by the operator enables the operator to readily ascertain whether or not the apertured metallic material 11 is acceptable by engineering standards.

In the case of aperture masks, material 11 represents one mask from an indefinite line having several located thereon. Removal of the mask for detection by inspection apparatus 11 thus provides the highly desirable capability of the production apparatus to periodically inspect the production line. Particularly with regard to aperture masks, the operator upon making his necessary comparison may then relate to the production line his results. Again with particular regard to aperture masks, the step immediately proceeding which resulted in the mask as illustrated involved chemical etching. Accordingly, the operator of inspection apparatus 10 relays the obtained information to the operator of the etching apparatus who in turn correspondingly manipulates his apparatus to either increase or decrease the amount of echtant and its respective flow rate to the respective areas on the mask line.

If the operator further desires a completed report of all readings as ascertained by apparatus 10, he in turn triggers station 39 to actuate typewriter 43. The typewriter then provides a complete typed report of the readings as displayed on the cathode ray tube of television 41.

With particular reference to FIG. 2, a more detailed view of the movable retention means 15 and the light determination means 13 is provided. Light source 19 preferably comprises a collimator means 44 which in turn receives light from a power source (not shown) through a tube 45 of fiber optic bundles. The mentioned power source is conveniently positioned within, but not operatively connected to, voltmeter 33. As previously stated, light detection means 21 is positioned on an opposing side of apertured metallic material 11 from light source 19 and is electrically joined to digital voltmeter 33. In the preferred embodiment of the invention, light detection means 21 comprises a phototube and precision resistor which are electrically energized upon receiving light thereto. This responsive signal is then provided digital voltmeter 33 which in turn provides the necessary first signal to computer 17.

As illustrated in FIG. 2, apertured metallic material 11 is positioned in a substantially planar relationship whereby the metallic material occupies a singular plane. This is achieved by magnetically attaching material 11 to a plurality of aligned retaining members 47. Each of the retaining members have therein a magnet 49 which serves to magnetically retain the metallic apertured material 11 thereto. It is to be understood that other means could be utilized to secure metallic material 11. However, it has been determined that the use of magnetic attraction to accomplish this purpose is more conducive to successful retention of the relatively thin apertured metallic material as typically found in aperture masks.

The aforementioned retaining members 47 are movably positioned on first movable frame member 27 in the manner illustrated. As can be seen, members 47 are positioned in a paired relationship with each pair being commonly joined by a common threaded shaft 51. Additionally, each pair is adapted for slidable movement on a corresponding parallel shaft 53. In turn, each shaft 51 is operatively connected through a common faceplate to an adjusting crank 55. It can be seen that by turning either of the cranks 55, the corresponding threaded shaft 51 will rotate. This in turn results in each of the illustrated pairs of retaining members moving either toward or away from each other in a spaced relationship, depending upon the direction of rotation of the respective cranks. This is further achieved by providing each of the bases 57 of each pair of retaining members 47 with reverse threading. Thus a means has been provided whereby the pairs of retaining members may be manually adjusted to in turn have the capability of being able to fixedly retain metallic materials of varying dimensions. As illustrated in FIG. 2, it is preferred to position the respective pairs of retaining members 47 in a vertical-horizontal relationship. It is to be understood that this is but a preferred method of positioning these members and is not meant in any manner to limit the present invention. That is, each of the pairs could be respectively offset from the horizontal or vertical axis. It is to be remembered, however, that the described positioning relationship of these pairs as illustrated is preferred when inspecting aperture masks. This is primarily because each mask is substantially rectangular in shape and the positioning of the mask is facilitated by securing the mask to retaining members 47 in the manner as described.

As further illustrated in FIG. 22, each of the pairs of retaining members 47 are secured to first movable frame 27. Frame 27, operatively connected to drive means 23, is in turn movably positioned on the second movable frame 29. As illustrated, second movable frame 29 is operatively connected to drive means 25. The aforementioned drive means are electrically joined to the described electrical buffer translators which in turn are electrically connected to computer 17 and adapted for receiving signals therefrom. The second movable frame 29 is movably positioned along a series of upstanding rails 61 which in turn are fixedly retained to an upstanding frame 63.

In accordance with the preferred embodiments of the invention, movable frame 27 is adapted for moving in a substantially horizontal direction upon being driven by drive means 23. Accordingly, movable frame 29 is adapted for being moved in a substantially vertical direction upon being driven by drive means 25. The aforementioned vertical-horizontal direction of movement of retention means 51 in turn facilitates movement of metallic material 11 in such a manner whereby selected areas along vertical and horizontal axis of the planar positioned material 11 can be read. Additionally, this direction of movement relationship further facilitates reading of the selected areas along linear projection lines established in diagonal relationships to the described vertical and horizontal axes.

Figure 3:
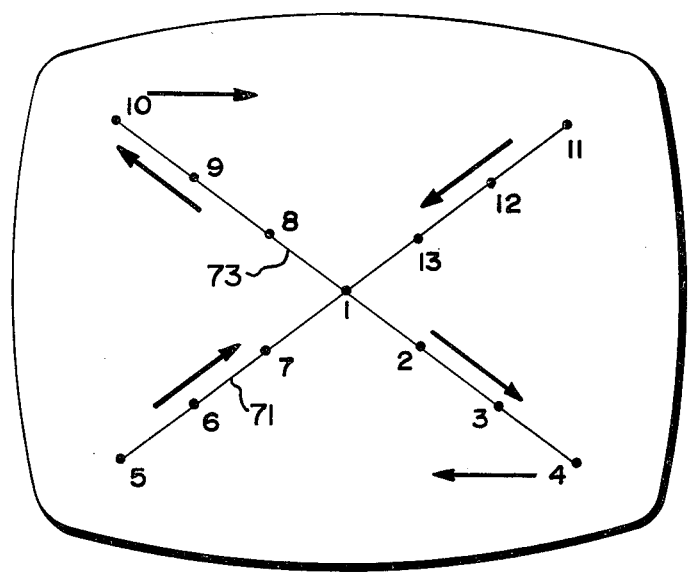
FIG. 3 illustrates the preferred pattern for detecting the selected areas on an apertured metallic material.
Figure 4:
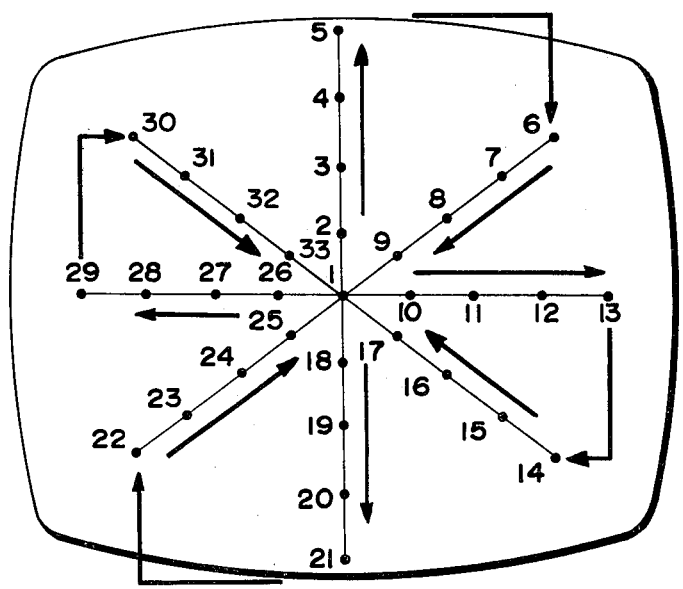
FIG. 4 illustrates a second preferred pattern for detecting areas on metallic material.

With particular reference to FIG. 3, a more detailed illustration of the preferred manner for inspecting apertured metallic material 11 is given. In accordance with the desired program as provided by computer 17, any predetermined selected areas can be sequentially inspected by apparatus 10. The total number of areas are determined from the aforementioned job number input to the control means from manual control station 39. Each of these areas, illustrated as a total of 13 in FIG. 3, consist of at least one aperture which is to be inspected to determine its relative size in comparison to acceptable standards. In the preferred operation of the invention, the first area to be read (indicated by numeral 1) is at the approximate center of material 11 as defined by at least two intersecting projection lines 71 and 73. The next area to be read is one (indicated by numeral 2) along one of these intersecting diagonals. Areas 3, 4, 5, etc. are next preferably inspected in accordance with the numerical order as shown. As illustrated, at least two linear projection lines 71 and 73 are utilized to provide the desired predetermined pattern of inspection. It is to be understood that should it be desirable to inspect additional areas at other strategic locations on material 11, additional areas on corresponding additional linear projections could easily be inspected. Such an example is illustrated in FIG. 4 wherein a total number of 4 linear projections are utilized to in turn provide a total inspection of at least 33 selected areas. It can be understood that the number of selected areas to be inspected is primarily dependent on the desired manufacturing standards for each size of material 11.

PREFERRED COMPONENTS OF THE INVENTION

As stated, the preferred component for control means 17 is an IBM Systems/7 electronic computer. Similarly, the preferred components for reporting means 37 and control station 39 are a No. 1053 electronic typewriter, printer model No. 4 and a No. 7414 control unit with function pad, respectively, also available from the IBM Corporation.

The preferred members of drive means 23 and 25 are model MO63-FC-06 SLO-SYN drive motors, available from the Superior Electric Co., Bristol, Connecticut. The described electric buffer translators adaptable for functioning with these motors are available under Model No. BTR105RT, also from Superior Electric. For output means 35, an RCA television receiver/monitor Model JR-345B is preferred.

Thus an apparatus and a method have been provided for automatically inspecting a plurality of selected areas of an apertured metallic material to determine the relative sizes of the apertures within the material.

While there has been shown and described what are at present considered the preferred embodiments of the invention, it will be obvious to those skilled in the art that various changes and modifications may be made therein without departing from the scope of the invention as defined by the appended claims.

What is claimed is:

1. An automated inspection apparatus for sequentially inspecting a plurality of selected areas of an apertured metallic material in accordance with a predetermined pattern to determine the relative sizes of the apertures within said material, said apparatus comprising:

light determination means including an established light source for projecting a collimated column of light to one side of said metallic material and a singular light detection means positioned on an opposing side of said metallic material substantially opposite said established light source for detecting the light from said light source passing through at least one of said apertures within each of said selected areas of said material;

movable retention mean for fixedly retaining said metallic material between said light source and said light detection means and for moving said metallic material to sequentially position each of said selected areas of said metallic material between said light source and light detection means in accordance with said predetermined pattern; and control means operatively connected to said light determination means and said movable retention means for automatically actuating said movable retention means and said light determination means in a pre-established manner to cause said movable retention means to move said metallic material in said predetermined pattern, said light source to project said collimated light to one side of each of said selected areas, and said singular light detection means to detect the light passing through said material at each of said selected areas when said selected areas are positioned between said light source and said singular light detection means in accordance with said predetermined pattern, said predetermined pattern comprising a planar pattern wherein said selected areas are spacedly positioned along a plurality of linear projections intersecting at a point substantially centrally located on said apertured material, the first of said areas to be inspected located at said centrally located point.

2. The inspection apparatus according to claim 1 wherein said movable retention means comprises first and second movable frame members each having a drive means operatively joined thereto for driving said frame members, each of said drive means operatively connected to said control means.

3. The inspection apparatus according to claim 2 further including a plurality of retaining members spacedly positioned on said first movable frame member for retaining said apertured metallic material.

4. The inspection apparatus according to claim 3 wherein each of said retaining members comprises a magnetic member for magnetically attaching to said apertured metallic material to thereby retain said material within said movable retention means.

5. The inspection apparatus according to claim 1 wherein said control means comprises an electronic computer, said computer electrically connected to said light determination means and said movable retention means and adapted for providing electrical signals thereto to cause said movable retention means to move said apertured metallic material in said predetermined pattern.

6. The inspection apparatus according to claim 5 wherein said light determination means further comprises a responsive means operatively connected to said light detection means for providing a first electrical signal upon detecting said light passing through each of said selected areas, said first electrical signal representative of the relative size of at least one of said apertures within each of said selected areas of said material.

7. The inspection apparatus according to claim 6 wherein said electronic computer is adapted for receiving said first electrical signal from said light determination means and for providing a second electrical signal representative of said first electrical signal.

8. The inspection apparatus according to claim 7 further including an output means electrically connected to said electronic computer, said output means adapted for receiving said second electrical signal and thereafter providing a visual output.

9. The inspection apparatus according to claim 5 further including a manually actuated control station electrically connected to said electronic computer for providing a means whereby a manually triggered input signal can be supplied to said computer prior to said moving of said aperture material in said predetermined pattern.

10. The inspection apparatus according to claim 6 wherein said responsive means comprises a digital voltmeter.

11. A method for sequentially inspecting a plurality of selected areas of an apertured metallic material in accordance with a predetermined pattern to determine the relative sizes of the apertures within said material utilizing an apparatus including a light determination means having an established light source and a positioned singular light detection means, and a movable retention means, said method comprising:

fixedly positioning said apertured metallic material on said movable retention means to cause said apertured metallic material to occupy a singular plane;

actuating said movable retention means to move said apertured metallic material in accordance with said predetermined pattern to cause each of said selected areas on said apertured metallic material to be sequentially positioned between said established light source and said positioned singular light detection means, said predetermined pattern comprising a planar pattern wherein said selected areas are spacedly positioned along a plurality of linear projections intersecting at a point substantially centrally located on said apertured material, the first of said areas to be inspected located at said centrally located point; and actuating said light determination means in a pre-established manner to cause said established light source to project a collimated column of light to one side of each of said selected areas and said singular light detection means to detect the light passing through said apertured metallic material at each of said selected areas when said selected areas are positioned between said light source and said singular light detection means.

12. The method according to claim 11 wherein the number of said linear projections intersecting at said substantially centrally located point on said apertured metallic material is two.

13. The method according to claim 12 wherein the number of said selected areas spacedly positioned along said two linear projections is thirteen.

14. The method according to claim 11 wherein the number of said linear projections intersecting at said substantially centrally located point on said apertured metallic material is four.

15. The method according to claim 14 wherein the number of said selected areas spacedly positioned along said four linear projections is thirty-three.

* * * * *